US006476271B2

(12) United States Patent
Van Der Puy

(10) Patent No.: US 6,476,271 B2
(45) Date of Patent: Nov. 5, 2002

(54) PROCESS FOR THE PREPARATION OF ETHER-FREE SALTS OF TETRAKIS (PENTAFLUOROPHENYL) BORATE

(75) Inventor: Michael Van Der Puy, Amherst, NY (US)

(73) Assignee: Honeywell International, Inc., Morristown, NJ (US)

( * ) Notice: Subject to any disclaimer, the term of this patent is extended or adjusted under 35 U.S.C. 154(b) by 0 days.

(21) Appl. No.: 09/860,398

(22) Filed: May 18, 2001

(65) Prior Publication Data

US 2001/0056202 A1 Dec. 27, 2001

Related U.S. Application Data

(60) Provisional application No. 60/212,588, filed on Jun. 19, 2000.

(51) Int. Cl.$^7$ .................................................. C07F 5/02
(52) U.S. Cl. ................................................ 568/6; 568/1
(58) Field of Search ............................................ 568/1, 6

(56) References Cited

U.S. PATENT DOCUMENTS

| 5,296,433 | A |  | 3/1994  | Siedle et al.    |         |
|-----------|---|--|---------|------------------|---------|
| 5,399,781 | A |  | 3/1995  | Doellein         |         |
| 5,420,355 | A |  | 5/1995  | Ikeda et al.     |         |
| 5,473,036 | A |  | 12/1995 | Piotrowski et al.|         |
| 5,488,169 | A |  | 1/1996  | Ikeda et al.     |         |
| 5,493,056 | A |  | 2/1996  | Ikeda et al.     |         |
| 5,545,759 | A |  | 8/1996  | Ikeda et al.     |         |
| 5,600,004 | A |  | 2/1997  | Diefenbach       |         |
| 5,600,005 | A |  | 2/1997  | Naganuma et al.  |         |
| 5,693,261 | A |  | 12/1997 | Krzystowczyk et al. |       |
| 5,693,867 | A |  | 12/1997 | Baur et al.      |         |
| 5,959,151 | A |  | 9/1999  | Lee et al.       |         |
| 6,162,950 | A | * | 12/2000 | Lee et al.      | 568/6   |
| 6,169,208 | B1 | * | 1/2001  | Lee et al.     | 568/6   |
| 6,231,790 | B1 | * | 5/2001  | Askham         | 260/665 G |

FOREIGN PATENT DOCUMENTS

| EP | 0 825 195 A1 | 2/1998 |
| EP | 0 913 400 A1 | 5/1999 |

OTHER PUBLICATIONS

Chien, et al., "Isospecific Polymerization of Propylene Catalyzed by rac– Ethylenebis(indenyl)methylzirconium 'Cation'", Am. Chem. Soc., 1991, pp. 8570–8571, vol. 113.

Massey, et al., "Perfluorophenyl Derivatives of the Elements I. Tris(pentafluorophenyl)boron", J. Organometal. Chem., 1964, pp. 245–250, vol. 2.

* cited by examiner

Primary Examiner—Jean F. Vollano
(74) Attorney, Agent, or Firm—Deborah Chess; Colleen Szuch

(57) ABSTRACT

A method is provided for making substantially ether-free alkali metal tetrakis(pentafluorophenyl) borate salts from tetrakis(pentafluorophenyl) borate magnesium bromide and converting the alkali metal tetrakis(pentafluorophenyl) borate salts to essentially ether-free trityl tetrakis (pentafluorophenyl) borate.

11 Claims, No Drawings

PROCESS FOR THE PREPARATION OF ETHER-FREE SALTS OF TETRAKIS (PENTAFLUOROPHENYL) BORATE

CROSS-REFERENCE TO RELATED APPLICATIONS

This application claims the benefit of U.S. Provisional Application No. 60/212,588, filed Jun. 19, 2000.

FIELD OF THE INVENTION

The present invention relates to methods for preparing tetrakis(pentafluorophenyl) borate salts used in conjunction with metallocene catalysts for olefin polymerization. More specifically, the present invention relates to novel methods for making trityl tetrakis(pentafluorophenyl) borate that is substantially free of ether and other oxygenated contaminants, and the tetrakis(pentafluorophenyl) borate salts used in its preparation.

BACKGROUND OF THE INVENTION

Boron co-catalysts and their metallocene catalyst counterparts are highly effective in the polymerization of ethylene and propylene. Both components of such catalyst systems need to be free of contaminants that would interfere with the polymerization process since they are used at very low levels, compared to the weight of the monomer used in the reaction. Such contaminants include Lewis bases (substances that donate a pair of electrons). Therefore, safe and reliable processes for the manufacture of high purity trityl tetrakis(pentafluorophenyl) borate are desirable. More preferred are manufacturing processes for trityl tetrakis (pentafluorophenyl) borate that provide a product having consistent color and high purity. It has been determined that, with respect to purity, it is most desirable for trityl tetrakis (pentafluorophenyl) borates to be substantially free of ether (less than 0.5 wt %) and other oxygenated contaminants such as water.

There are few known methods for making trityl tetrakis (pentafluorophenyl) borate. One method, as described in U.S. Pat. No. 5,399,781, involves reacting lithium tetrakis (pentafluorophenyl) borate with trityl chloride in an alkane. This process yields, at least in part, trityl tetrakis (pentafluorophenyl) borate. Further, such processes described in the U.S. Pat. No. 5,399,781 patent can be achieved in the absence of ether solvents. In addition, the process for making the required starting material lithium tetrakis(pentafluorophenyl) borate can also be achieved in the absence of ether solvents. However, pentafluorophenyl lithium, from which lithium tetrakis(pentafluorophenyl) borate is made, is hazardous and must therefore be handled at low temperatures. This significantly complicates the process, ultimately affecting process costs. Thus, while suitable for small-scale laboratory operations, the above-described lithium tetrakis synthesis is not desirable for large-scale manufacture.

Sodium and potassium tetrakis(pentafluorophenyl) borates are known. The use of these materials for the preparation of trityl tetrakis(pentafluorophenyl) borate is suggested in EP 0 913 400 A1, although no experimental data was provided specifically for the preparation of the trityl borate. One method of preparing the potassium salt is known (A. G. Massey and A. J. Park, *J. Organometallic Chem.*, 2 (1964) 245), but again, this method utilizes the lithium salt. Therefore, for the reasons already explained above, this method offers no better solution to the problem.

Mitsui et al. (EP 0 913 400 A1, 1999) describe the conversion of $(C_6F_5)_4BMgBr$ into the corresponding sodium salt. The bromomagnesium salt can be made more safely by using the Grignard reagent, $C_6F_5MgBr$. However, the conversion of the magnesium salt to the corresponding alkali metal borates involves treating the magnesium salt (in ether-toluene) with an aqueous solution of a sodium carboxylate, and extracting the aqueous layer with ethyl acetate. Although the purity of the desired sodium salt was acceptable according to fluorine NMR analysis, no indication was given as to the presence of residual solvents in the product.

In addition to the hazards associated with the use of pentafluorophenyl lithium, the crude mixture of LiCl and trityl tetrakis(pentafluorophenyl) borate was described in the prior art as a yellow solid. However, after removing the LiCl, the supposedly "purified" product was not yellow, but was orange in color (an observation also made by Chien et al. who used the same process (*J. Am. Chem. Soc.*, 113 (1991) 8570)). The change in color from yellow to orange in these prior art preparations of trityl tetrakis (pentafluorophenyl) borate is taken as an indication of the presence of the residual polar materials in the final product.

Prior art preparations of solid trityl tetrakis (pentafluorophenyl) borate have been isolated by removing methylene chloride solvent from the borate solution. If the removal of the last amount of the methylene chloride is vacuum assisted, the product tends to "bloom" or foam up, filling the entire vessel. Once the solvent is removed, the foamed trityl product is difficult to remove from the reaction vessel. This foaming inhibits the use of this process on a large scale.

As shown below in the Comparative Example section, when sodium tetrakis(pentafluorophenyl) borate is made according to EP 0 913 400 A1, ethyl acetate is clearly present as evidenced by proton NMR analysis. This illustrates the difficulty of removing coordinating contaminants from tetrakis(pentafluorophenyl) borate salts. In fact, this European patent discloses many ether complexes of borate salts, again indicative of the strong bond between the borate salts and ethers.

Thus, a safe, repeatable, and scaleable method for preparing trityl tetrakis(pentafluorophenyl) borate of consistent color and purity, while being essentially free of ether and other oxygen contaminants, is not known.

SUMMARY OF THE INVENTION

In accordance with one embodiment, the present invention relates to producing sodium or potassium tetrakis (pentafluorophenyl) borate that is substantially free of ether and other organic contaminants containing oxygen atoms. In a second embodiment, the invention relates to a method for producing trityl tetrakis(pentafluorophenyl) borate from the corresponding alkali metal salt.

More specifically, the present invention relates to a method for making lithium, sodium or potassium tetrakis (pentafluorophenyl) borate that is substantially free of ether and other organic contaminants containing oxygen atoms from a pentafluorophenyl magnesium bromide compound. Preferably, the (pentafluorophenyl) magnesium bromide is reacted in an ether solvent with a tris(pentafluorophenyl) borane in an aromatic hydrocarbon solvent to produce tetrakis(pentafluorophenyl) borate magnesium bromide. The tetrakis(pentafluorophenyl) borate magnesium bromide is then reacted with an aqueous solution of a halide selected from the group consisting of sodium chloride and potassium chloride to create an organic phase containing a product compound selected from the group consisting of tetrakis (pentafluorophenyl) borate sodium salt and tetrakis (pentafluorophenyl) borate potassium salt. The organic phase is separated, and the solvent is removed from the organic phase to provide a substantially ether-free compound selected from the group consisting of sodium tetrakis (pentafluorophenyl) borate and potassium tetrakis (pentafluorophenyl) borate. Most preferably, the product compound comprises less than about 0.5 weight percent ether.

In accordance with a further embodiment, the present invention relates to the manufacture of trityl tetrakis (pentafluorophenyl) borate by first providing a substantially ether-free compound selected from the group consisting of sodium tetrakis(pentafluorophenyl) borate and potassium tetrakis(pentafluorophenyl) borate. The substantially ether-free compound is then reacted with a trityl halide in a hydrocarbon liquid to form a slurry of trityl tetrakis (pentafluorophenyl) borate and a halide in a hydrocarbon liquid. The trityl tetrakis(pentafluorophenyl) borate and halide is then separated from the hydrocarbon liquid by a suitable method, such as filtration or decantation, followed by dissolving the trityl tetrakis(pentafluorophenyl) borate in a halogenated solvent to form a solution, said solvent not containing oxygen, nitrogen or other coordinating atoms. The trityl tetrakis(pentafluorophenyl) borate solution is then diluted in a hydrocarbon solvent having a higher boiling point than the halogenated solvent. Finally, the halogenated solvent and the hydrocarbon solvent are removed to provide pure trityl tetrakis(pentafluorophenyl) borate product. Most preferably, the product compound comprises less than about 0.1 weight percent ether.

DETAILED DESCRIPTION OF THE INVENTION

In a more preferred embodiment, the present invention relates to manufacturing compounds having the formula $(C_6F_5)_4BM$, wherein M=Na or K, by first reacting pentafluorophenyl magnesium bromide in ether with tris (pentafluorophenyl) borane in an aromatic hydrocarbon (e.g. toluene, xylene, or ethylbenzene, and preferably toluene) at a temperature from about 20 to about 65° C. to produce tetrakis(pentafluorophenyl) borate magnesium bromide. The mixture of tetrakis(pentafluorophenyl) borate magnesium bromide and solvent is reacted with an aqueous solution of sodium chloride or potassium chloride. During this step of the process, the $(MgBr)^+$ cation in the borate salt is exchanged for $Na^+$ or $K^+$. The amount of NaCl or KCl used should be at least one mole per mole of tetrakis (pentafluorophenyl) borate magnesium bromide. Preferably, it is more than this so as to ensure a high degree of the desired exchange. Thus, an amount of from about 1 to about 20 molar equivalents may be used, and more preferably, from about 5 to about 10 molar equivalents. Sodium and potassium tetrakis(pentafluorophenyl) borate have good solubility in ether-toluene mixtures. The magnesium salts (e.g., $MgBrCl$) dissolve in the aqueous layer. This reaction is fairly rapid at room temperature and is complete in from about 15 to about 60 minutes with stirring. The two resultant phases are distinct and easily separated.

The organic phase which contains sodium tetrakis (pentafluorophenyl) borate or potassium tetrakis (pentafluorophenyl) borate is separated from the aqueous phase. Solvent is then removed in such a way as to provide substantially ether-free sodium tetrakis(pentafluorophenyl) borate or potassium tetrakis(pentafluorophenyl) borate. It is understood that the term "substantially ether-free" refers to an ether content in the salt of less than about 5.0 weight percent, preferably less than about 3.0 weight percent, and more preferably less than about 1.0 weight percent. In order to achieve this, ether is removed by atmospheric distillation. The head temperature during the distillation must be as close to the boiling point of the aromatic hydrocarbon as possible at atmospheric pressure before the ether distillation is considered complete. For example, when toluene is the aromatic hydrocarbon, the further the head temperature is from the normal boiling point for toluene of 110° C., the higher will be the ether content in the borate salt. To achieve an ether content in the borate salt of less than about 0.5 weight %, the head temperature during the distillation should not be less than about 109° C. Surprisingly, when treated similarly, tetrakis(pentafluorophenyl) borate magnesium bromide is not rendered ether free. To isolate sodium or potassium tetrakis(pentafluorophenyl) borate, ether may be distilled from the other components. Upon cooling, the borate salt will precipitate out of solution and may be removed by filtration. Alternatively, toluene may be removed by distillation at atmospheric pressure or, preferably, under vacuum, to provide the borate salt.

In accordance with a further preferred embodiment, the present invention relates to the manufacture of trityl tetrakis (pentafluorophenyl) borate. A slurry of substantially ether-free tetrakis(pentafluorophenyl) sodium borate is reacted with trityl chloride in a hydrocarbon of six to ten carbons, preferably a non-aromatic hydrocarbon, more preferably heptane, to form a slurry of trityl tetrakis(pentafluorophenyl) borate and sodium chloride in heptane. The reaction occurs slowly at room temperature, but is more efficiently accomplished at reflux (about 98° C.) for a period of from about 0.5 to about 10 hours, and more preferably from about 1 to about 3 hours. The amount of trityl chloride used should be at least one mole of trityl chloride per mole of sodium salt, but a slight excess is preferred (from about 1.05 to about 3 equivalents and more preferably from about 1.1 to about 1.6 equivalents). The solid products are removed from the heptane by a suitable method, such as filtration or decantation. Trityl tetrakis(pentafluorophenyl) borate is then selectively dissolved in a halogenated solvent that does not contain oxygen, nitrogen, or other coordinating atoms. Appropriate solvents are selected from the halogenated solvents selected from the group consisting of methylene chloride($CH_2Cl_2$), chloroform ($CHCl_3$), carbon tetrachloride ($CCl_4$) and trichlorotrifluoroethane ($CF_3CCl_3$). The trityl tetrakis(pentafluorophenyl) borate solution is then diluted with a hydrocarbon solvent having a higher boiling point than the halogenated solvent, such as heptane, followed by distillation to remove all organic solvents to provide essentially ether-free, yellow, trityl tetrakis (pentafluorophenyl) borate. It is understood, that the term "essentially ether-free" refers to an ether content in the final trityl tetrakis(pentafluorophenyl) borate of less than about 0.5 weight percent, preferably less than about 0.3 weight percent, and more preferably less than about 0.1 weight percent. Therefore the process of the present invention produces, for the first time, a solid, ether-free trityl tetrakis (pentafluorophenyl) borate that is yellow in color (as opposed to the known orange color).

Surprisingly, the sodium borate salt used in the preparation of the trityl borate salt may contain small amounts of ether and/or water, which will not be transferred to the trityl salt using the preferred embodiments of this invention. The ether content of the sodium salt should not exceed about 3.0 weight percent, is preferably about less than about 1.0 weight percent, and still more preferably it should not exceed about 0.5 weight percent. The limits on amount of water present are similar. Exceeding the preferred limits may not prevent the formation of the trityl borate salt, but if exceeded, water and ether may be present in the final trityl borate product. It is understood that the presence of water will then require a separate step to remove it. Drying over molecular sieves has been ineffective, but chemical drying can be used.

As stated above, known prior methods for manufacture of the desired product result in foaming or blooming, which is disadvantageous. According to the present invention, to isolate solid product without "blooming", a hydrocarbon solvent comprising a six to ten carbon hydrocarbon compound is added to the halogenated solvent to create a solvent mixture. The solvent is then distilled off to give a slurry of the borate in the hydrocarbon solvent which is then filtered. Therefore, the process of the present invention not only produces an ether-free form of the desired trityl tetrakis(pentafluorophenyl) borate, but the borate is produced for the first time as a yellow product, and is synthesized in an efficient manner in high purity without wasteful "blooming" or foaming.

Further objects and advantages of the present invention are further illustrated by the following examples, but the particular materials and amounts recited in these examples as well as other conditions and details should not be construed to unduly limit the invention.

EXAMPLE 1
Preparation of sodium tetrakis(pentafluorophenyl) borate

In one vessel, 18.3 g (0.0357 mol) of tris(pentafluorophenyl)borane (99% pure) was dissolved in 100 mL of dry toluene. In another vessel, pentafluorophenyl magnesium bromide in dry diethyl ether was prepared as follows. To 0.881 g (0.0363 mol) Mg under 65 mL ether was added 0.6 ethyl bromide, and the mixture stirred for 0.5 hour. Bromopentafluorobenzene (8.9 g, 0.0360 mol) was then added at 25° C. over a period of 80 minutes. Stirring was continued for 1 hour longer to allow all of the magnesium to react. The Grignard solution was added to the solution of tris(pentafluorophenyl)borane in toluene, and the mixture heated to 60° C. for 5 hours, forming the bromomagnesium salt of tetrakis(pentafluorophenyl) borate. Upon cooling to room temperature, two phases formed. The magnesium tetrakis salt was converted via cation exchange into the corresponding sodium salt (sodium tetrakis(pentafluorophenyl) borate), by adding a solution of 20 g NaCl in 100 mL water (slowly at first due to the exothermic hydrolysis) and stirring for 1 hour. The phases were separated and the aqueous phase extracted with 50 mL ether. The combined organic phases were dried ($MgSO_4$). Most of the solvent was removed by distillation at atmospheric pressure, up to a head temperature of 108° C., and the remainder under vacuum to give 18.1 g tan sodium salt (0.0258 mol, 72% yield). $^1$H NMR analysis indicated 3.0 weight % ether. $^{19}$F NMR (DMSO-$d_6$): −130 (8 F), −159 (4 F), and −163.5 (8 F) ppm.

A 12.8-gram portion of the above sodium salt was combined with 35 mL of dry toluene, and atmospheric distillation was conducted until the head temperature was 110° C. and about 10 mL distillate had been collected. The pot contents were then taken to dryness under vacuum at a maximum temperature of 60° C. The solid so obtained was analyzed by $^1$H NMR. Ether was barely detectable (<0.35% by weight).

EXAMPLE 2
Preparation of ether-free potassium tetrakis(pentafluorophenyl) borate The bromomagnesium salt of tetrakis(pentafluorophenyl) borate was made in a manner similar to that described in Example 1. Pentafluorophenyl magnesium bromide (0.055 mol) in 80 mL ether was added to 26.9 g (0.0525 mol) of $(C_6F_5)_3B$ in 125 mL toluene. The mixture was stirred at 42° C. for 48 hours, at which time the reaction was essentially complete, as determined by NMR analysis. A solution of 30 g KCl in 100 mL water was added over 10 minutes, keeping the temperature below 30° C. The layers were separated and the aqueous layer extracted with 75 mL ether. The combined organic layers were then distilled up to a head temperature of 109° C. and 205 mL distillate was collected. The remainder of toluene was removed under vacuum to give 26.6 g of a tan, free-flowing powder. Analysis indicted ether in an amount less than 0.35 wt %, although water was still present.

EXAMPLE 3
Preparation of trityl tetrakis(pentafluorophenyl) borate from sodium tetrakis(pentafluorophenyl) borate Sodium tetrakis(pentafluorophenyl) borate (32.4 g, 0.046 mol), prepared in the manner described in Example 1, was combined with 16.5 g (0.0592 mol) of trityl chloride and 302 mL (206.6 g) of heptane. The mixture was refluxed for 3 hours, with provision made to distill off any water that might be present. The yellow slurry was cooled, and 245 mL heptane was decanted (to remove excess trityl chloride). An additional 150 mL heptane was added, followed by stirring and decanting 155 mL. Residual heptane was then removed, and the solid treated with 150 mL dry $CH_2Cl_2$. The slurry was then filtered through a celite pad, which was washed twice with 25 mL $CH_2Cl_2$. All but 40 mL of the $CH_2Cl_2$ was removed by distillation. Then, 90 mL heptane was added and removal of solvent was continued, using vacuum to remove the last traces of heptane. There was obtained 34.3 g (0.0372 mol) of canary yellow trityl salt (81% yield from the sodium salt, 63% from tris(pentafluorophenyl)borane). Its purity was determined by $^{19}$F NMR (−132.8, −163.3, and −167.2 ppm) to be essentially 100% and by $^1$HNMR(8.27, 7.89, and 7.71 ppm) to be 97.2%, of which 1.7% was heptane. Ether was not detected by NMR.

EXAMPLE 4
Preparation of dry trityl tetrakis(pentafluorophenyl) borate from sodium tetrakis(pentafluorophenyl) borate containing about 3.5% water Sodium tetrakis(pentafluorophenyl) borate (11.9 g, 0.017 mol) prepared according to Example 1 was analyzed by proton NMR and found to contain 3.5 wt % water and <0.4 wt % ether. It was combined with 150 mL heptane and 6.0 g (0.022 mol) trityl chloride and the resulting slurry was heated to reflux for 4 hours, with provision made to remove any water via a distillation take-off head (about 10 mL of wet heptane was distilled off). After cooling the mixture and allowing solids to settle, the bulk of the heptane was decanted off. Fresh heptane (100 mL) was added, and after stirring and allowing the mixture to settle, most of the heptane was again decanted. The remaining heptane was removed under vacuum to give a yellow solid. Methylene chloride (80 mL) $CH_2Cl_2$ was added and the slurry filtered with suction through a celite pad. The volume of the filtrate was reduced to about 35 mL, and 40 mL heptane was added, resulting in 2 liquid phases. Methylene chloride was removed by distillation, leaving a slurry of yellow trityl tetrakis(pentafluorophenyl) borate. Finally, heptane was removed under vacuum to give the product as a free flowing, yellow powder. The total proton NMR spectrum was integrated, except for the NMR solvent. Of the total integrated area, 97.4% was attributed to trityl tetrakis (pentafluorophenyl) borate, 1.17% to heptane, and 1.48% to unknown material. Both water and ether were absent.

EXAMPLE 5
Conversion of orange trityl tetrakis(pentafluorophenyl) borate into yellow trityl tetrakis(pentafluorophenyl) borate Orange crystals of trityl tetrakis(pentafluorophenyl) borate were prepared using a procedure involving, in the last step, removing $CH_2Cl_2$ from purified material (i.e., free of inorganic salts). The material was re-dissolved in a minimum amount of $CH_2Cl_2$, and twice the volume of heptane was added. The mixed solvents were then removed under vacuum to give trityl tetrakis(pentafluorophenyl) borate as a yellow solid.

EXAMPLE 6
Removal of water from wet trityl tetrakis (pentafluorophenyl) borate A 7.8-gram sample of trityl tetrakis(pentafluorophenyl) borate was prepared which contained approximately 1.2% by weight of water as determined by proton NMR. To this material was added 20 mL of $CH_2Cl_2$, 40 mL of heptane, and 1.2 g trityl chloride. The mixture was brought to reflux (50° C.) under a nitrogen atmosphere for about 1 hour. During this time, acid gas (HCl) evolution was noted. After cooling the mixture to room temperature, the dark supernatant liquid was separated. The solid was washed with 20 mL of heptane which was again decanted. Residual heptane was removed under vacuum to give 7.3 grams of yellow trityl tetrakis (pentafluorophenyl) borate having no detectable water by NMR analysis. No impurities were seen by fluorine NMR.

Comparative Example 1
Attempted preparation of ether free bromomagnesium salt of tetrakis(pentafluorophenyl) borate Pentafluorophenyl magnesium bromide was made as described in Example 1 using 0.681 g (0.028 mol) Mg, 0.4 g ethyl bromide, and 7.0 g (0.028 mol) $C_6F_5Br$ in 50 mL ether. The Grignard solution was added to 13.8 g (0.027 mol) of 99% pure $(C_6F_5)_3B$ in 65 mL toluene. After stirring for 20 hours at room temperature, the mixture was heated to 60–65° C. for 5 hours. An additional 50 mL toluene was added, and solvent was distilled out until the head temperature was 110° C. (the boiling point of toluene) and 62 mL of distillate had been collected. Upon cooling the pot contents, two liquid layers were present. The lower oily layer (22.2 grams) contained the bulk of the desired $(C_6F_5)_4BMgBr$. NMR analysis of this layer indicated a purity greater than 96% by fluorine NMR, but by proton NMR, ether was present in addition to toluene. The amount of ether in the lower oily layer was quantified using pentafluorotoluene as an internal standard and was found to be 18.3% by weight.

Comparative Example 2.
Preparation of sodium tetrakis(pentafluorophenyl) borate This is essentially the method of EP 913 400 A1. Pentafluorophenyl magnesium bromide (0.0323 mol) in 50 mL ether (prepared as described in Example 1) was added to 15.6 g of 99% pure $(C_6F_5)_3B$ in 65 mL ether. The mixture was stirred at 33° C. for 16 hours. Toluene (100 mL) was then added, with stirring and heating continued for 3 hours at 60–65° C. Analysis by $^{19}F$ NMR indicated complete reaction at this time and a good selectivity for a tetrakis (pentafluorophenyl) borate salt. A solution of 10 g sodium acetate in 100 mL water was added to the cooled mixture. After stirring 45 minutes, the aqueous phase was separated and extracted with 50 mL ethyl acetate. The combined organic layers were dried ($MgSO_4$) and filtered to provide a clear, light amber solution. Volatile materials were then removed under vacuum, including a final period of 45 minutes at 60° C. at a pressure of <1 mm Hg. Analysis of the residue (22.6 g) by $^1H$ NMR showed ethyl acetate (believed to be a complex of ethyl acetate and sodium tetrakis (pentafluorophenyl) borate).

The method of the present invention obtains an ether-free trityl tetrakis(pentafluorophenyl) borate from a sodium salt. Small amounts of ether present in the sodium salt by-product are not transferred to the trityl salt. The preferred methods of the present invention do not require sodium salt to be totally anhydrous to obtain anhydrous trityl salt. The process of the present invention is extremely efficient and convenient. In particular, the process of the present invention requires fewer processing safeguards than methods currently being used to make trityl tetrakis(pentafluorophenyl) borate.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for preparing sodium or potassium tetrakis (pentafluorophenyl) borate compound from a pentafluorophenyl magnesium bromide comprising the steps of:
   reacting the (pentafluorophenyl) magnesium bromide in an ether with a tris(pentafluorophenyl) borane in an aromatic hydrocarbon solvent to produce tetrakis (pentafluorophenyl) borate magnesium bromide;
   reacting the tetrakis(pentafluorophenyl) borate magnesium bromide with an aqueous solution of a halide selected from the group consisting of sodium chloride and potassium chloride to create an organic phase containing a product compound selected from the group consisting of tetrakis(pentafluorophenyl) borate sodium salt and tetrakis(pentafluorophenyl) borate potassium salt;
   separating the organic phase; and
   removing solvent from the organic phase to provide a substantially ether-free compound selected from the group consisting of sodium tetrakis(pentafluorophenyl) borate and potassium tetrakis(pentafluorophenyl) borate.

2. The method according to claim 1, wherein the product compound comprises less than about 5.0 weight percent ether.

3. The method according to claim 1, wherein the product compound comprises less than about 3.0 weight percent ether.

4. The method according to claim 1, wherein the product compound comprises less than about 1.0 weight percent ether.

5. The method according to claim 1 further comprising, after step (a), the step of removing the ether for recycling.

6. The method according to claim 1 wherein the aromatic hydrocarbon is selected from the group consisting of xylene, ethylbenzene, and toluene.

7. The method according to claim 3, wherein the aromatic hydrocarbon is toluene.

8. The method according to claim 1, wherein the (pentafluorophenyl)magnesium bromide is reacted with the tris(pentafluorophenyl) borane at a temperature of from about 20 to about 65° C.

9. The method according to claim 1, wherein (pentafluorophenyl)magnesium bromide is reacted in a mixture comprising ether and toluene.

10. The method according to claim 9, wherein said ether is diethyl ether and is first removed from the organic phase by distilling the organic phase until a temperature about equal to the boiling point of toluene at atmospheric pressure is achieved.

11. The method according to claim 1, wherein said ether is diethyl ether and wherein the solvent is removed from the organic phase by distilling the organic phase until a temperature of about 110° C. at atmospheric pressure is achieved.

* * * * *